(12) United States Patent
Biltz et al.

(10) Patent No.: US 9,763,814 B2
(45) Date of Patent: Sep. 19, 2017

(54) ELONGATE MEDICAL DEVICE

(71) Applicant: Cook Medical Technologies LLC, Bloomington, IN (US)

(72) Inventors: Benjamin T. Biltz, Spencer, IN (US); Bryan Baumann, Edgewood, KY (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/881,836

(22) Filed: Oct. 13, 2015

(65) Prior Publication Data

US 2016/0113787 A1   Apr. 28, 2016

Related U.S. Application Data

(60) Provisional application No. 62/068,067, filed on Oct. 24, 2014.

(51) Int. Cl.
  *A61F 2/88* (2006.01)
  *A61F 2/94* (2013.01)
  (Continued)

(52) U.S. Cl.
  CPC .................. *A61F 2/88* (2013.01); *A61F 2/94* (2013.01); *A61M 27/008* (2013.01); *A61F 2/07* (2013.01);
  (Continued)

(58) Field of Classification Search
  CPC ............ A61F 2/04; A61F 2/06; A61M 27/008
  (Continued)

(56) References Cited

U.S. PATENT DOCUMENTS 2,264,988 A  12/1941  Lee
3,514,791 A   6/1970  Sparks
(Continued)

FOREIGN PATENT DOCUMENTS

CA  2 264 988 A1  3/1999
DE    3314755 A1  4/1983
(Continued)

OTHER PUBLICATIONS

Hildebrandt, P., et al., Prevention of surface encrustation of urological implants by coating with inhibitors, Biomaterials 22 (2001) pp. 503-507.
(Continued)

*Primary Examiner* — Suzette J Gherbi
(74) *Attorney, Agent, or Firm* — Brinks Gilson & Lione

(57) ABSTRACT

An elongate medical device is provided. The device includes an elongate member defining a lumen through proximal, central, and distal portions. The central portion of the elongate member is defined from a plurality of closely aligned coils that establish the lumen within the central portion. The central portion further comprises a jacket disposed around a majority of an outer circumference of the plurality of coils, the jacket defining opposing first and second longitudinal edges that extend along the length of the central portion, and an elongate gap between opposing first and second longitudinal edges exposing portions of each of the plurality of coils aligned therewith, wherein the elongate gap allows for fluid communication from within or into the lumen through spaces between neighboring coils and through the elongate gap.

20 Claims, 8 Drawing Sheets

(51) Int. Cl.
*A61M 27/00* (2006.01)
*A61F 2/07* (2013.01)
*A61F 2/04* (2013.01)

(52) U.S. Cl.
CPC . *A61F 2002/048* (2013.01); *A61F 2210/0014* (2013.01); *A61F 2210/0076* (2013.01)

(58) Field of Classification Search
USPC .................................. 623/2.366–23.7; 604/8
See application file for complete search history.

(56) References Cited

U.S. PATENT DOCUMENTS

| | | |
|---|---|---|
| 4,003,369 A | 1/1977 | Heilman et al. |
| 4,080,706 A | 3/1978 | Heilman et al. |
| 4,295,464 A | 10/1981 | Shihata |
| 4,299,226 A | 11/1981 | Banka |
| 4,581,019 A | 4/1986 | Curelaru et al. |
| 4,666,442 A | 5/1987 | Arru et al. |
| 4,693,242 A | 9/1987 | Biard |
| 4,713,049 A | 12/1987 | Carter |
| 4,738,666 A | 4/1988 | Fuqua |
| 4,787,884 A | 11/1988 | Goldberg |
| 4,813,925 A | 3/1989 | Anderson, Jr. et al. |
| 4,820,262 A | 4/1989 | Finney |
| 4,913,683 A | 4/1990 | Gregory |
| 4,930,496 A | 6/1990 | Bosley, Jr. |
| 4,931,037 A | 6/1990 | Wetterman |
| 4,957,479 A | 9/1990 | Roemer |
| 4,994,033 A | 2/1991 | Shockey et al. |
| 5,044,369 A | 9/1991 | Sahota |
| 5,092,871 A | 3/1992 | Aebischer et al. |
| 5,160,341 A | 11/1992 | Brenneman et al. |
| 5,234,456 A | 8/1993 | Silvestrini |
| 5,254,104 A | 10/1993 | Furlow et al. |
| 5,323,768 A | 6/1994 | Saito et al. |
| 5,334,185 A | 8/1994 | Giesy et al. |
| 5,359,991 A | 11/1994 | Takahashi et al. |
| 5,370,691 A | 12/1994 | Samson |
| 5,405,334 A | 4/1995 | Roth et al. |
| 5,441,516 A | 8/1995 | Wang et al. |
| 5,545,213 A | 8/1996 | Keogh |
| 5,554,189 A | 9/1996 | De La Torre |
| 5,558,643 A | 9/1996 | Samson et al. |
| 5,582,619 A | 12/1996 | Ken |
| 5,601,591 A | 2/1997 | Edwards et al. |
| 5,643,254 A | 7/1997 | Scheldrup et al. |
| 5,681,274 A | 10/1997 | Perkins et al. |
| 5,690,667 A | 11/1997 | Gia |
| 5,766,192 A | 6/1998 | Zacca |
| 5,865,723 A | 2/1999 | Love |
| 5,964,744 A | 10/1999 | Balbierz et al. |
| 6,033,413 A | 3/2000 | Mikus et al. |
| 6,096,034 A | 8/2000 | Kupiecki et al. |
| 6,120,522 A | 9/2000 | Vrba et al. |
| 6,162,231 A | 12/2000 | Mikus et al. |
| 6,254,592 B1 | 7/2001 | Samson et al. |
| 6,264,611 B1 | 7/2001 | Ishikawa et al. |
| 6,280,457 B1 | 8/2001 | Wallace et al. |
| 6,332,892 B1 | 12/2001 | Desmond et al. |
| 6,371,979 B1 | 4/2002 | Beyar et al. |
| 6,383,146 B1 | 5/2002 | Klint |
| 6,395,021 B1 | 5/2002 | Hart et al. |
| 6,458,119 B1 | 10/2002 | Berenstein et al. |
| 6,517,569 B2 | 2/2003 | Mikus et al. |
| 6,582,472 B2 | 6/2003 | Hart |
| 6,589,262 B1 | 7/2003 | Honebrink et al. |
| 6,652,536 B2 | 11/2003 | Mathews et al. |
| 6,654,536 B2 | 11/2003 | Battey et al. |
| 6,685,744 B2 | 2/2004 | Gellman et al. |
| 6,702,846 B2 | 3/2004 | Mikus et al. |
| 6,733,536 B1 | 5/2004 | Gellman |
| 6,736,839 B2 | 5/2004 | Cummings |
| 6,746,489 B2 | 6/2004 | Dua et al. |
| 6,770,101 B2 | 8/2004 | Desmond, III et al. |
| 6,887,215 B2 | 5/2005 | McWeeney |
| 7,044,981 B2 | 5/2006 | Liu et al. |
| 7,087,661 B1 | 8/2006 | Alberte et al. |
| 7,108,655 B2 | 9/2006 | Whalen et al. |
| 7,412,993 B2 | 8/2008 | Tzeng |
| 7,550,012 B2 | 6/2009 | Lavelle |
| 7,637,863 B2 | 12/2009 | Deal et al. |
| 7,731,676 B2 | 6/2010 | Maeda |
| 7,731,693 B2 | 6/2010 | Melsheimer |
| 7,789,915 B2 | 9/2010 | Lavelle et al. |
| 7,811,238 B2 | 10/2010 | Melsheimer et al. |
| 7,914,809 B2 | 3/2011 | Atanasoska et al. |
| 7,946,999 B2 | 5/2011 | Rooney et al. |
| 7,959,554 B2 | 6/2011 | McAlexander et al. |
| 8,022,331 B2 | 9/2011 | Reynolds et al. |
| 8,137,291 B2 | 3/2012 | Melsheimer |
| 8,211,118 B2 | 7/2012 | Catanese, III et al. |
| 2001/0018574 A1 | 8/2001 | Toledo et al. |
| 2002/0002382 A1 | 1/2002 | Wallace et al. |
| 2002/0138129 A1 | 9/2002 | Armstrong et al. |
| 2002/0183852 A1 | 12/2002 | McWeeney |
| 2003/0018306 A1 | 1/2003 | Bucay-Couto et al. |
| 2003/0153971 A1 | 8/2003 | Chandrasekaran |
| 2004/0078088 A1 | 4/2004 | Gellman |
| 2004/0087886 A1 | 5/2004 | Gellman |
| 2004/0093075 A1 | 5/2004 | Kuehne |
| 2004/0127918 A1 | 7/2004 | Nikolchev et al. |
| 2004/0181186 A1 | 9/2004 | Gellman et al. |
| 2004/0193141 A1 | 9/2004 | Leopold |
| 2004/0267213 A1 | 12/2004 | Knapp |
| 2005/0033403 A1 | 2/2005 | Ward et al. |
| 2005/0075538 A1 | 4/2005 | Banik et al. |
| 2005/0222581 A1 | 10/2005 | Fischer, Jr. et al. |
| 2005/0234388 A1 | 10/2005 | Amos et al. |
| 2005/0240278 A1 | 10/2005 | Aliski et al. |
| 2006/0079926 A1 | 4/2006 | Desai et al. |
| 2006/0095050 A1 | 5/2006 | Hartley et al. |
| 2006/0135981 A1 | 6/2006 | Lenker et al. |
| 2006/0149359 A1 | 7/2006 | Richter et al. |
| 2006/0178739 A1 | 8/2006 | Shalaby et al. |
| 2007/0005024 A1 | 1/2007 | Weber et al. |
| 2007/0021840 A1 | 1/2007 | Lopera |
| 2007/0050006 A1 | 3/2007 | Lavelle |
| 2007/0078446 A1 | 4/2007 | Lavelle |
| 2007/0078511 A1 | 4/2007 | Ehr et al. |
| 2007/0123842 A1 | 5/2007 | Teague et al. |
| 2007/0161967 A1 | 7/2007 | Fischer, Jr. et al. |
| 2007/0191767 A1 | 8/2007 | Hennessy et al. |
| 2007/0250149 A1 | 10/2007 | Von Oepen et al. |
| 2007/0276466 A1 | 11/2007 | Lavelle et al. |
| 2008/0086215 A1 | 4/2008 | St. Pierre |
| 2008/0133025 A1 | 6/2008 | Daignault et al. |
| 2008/0183299 A1 | 7/2008 | Monga et al. |
| 2008/0208083 A1 | 8/2008 | Lin et al. |
| 2009/0105719 A1 | 4/2009 | Honey et al. |
| 2009/0326647 A1 | 12/2009 | Quillin |
| 2010/0057189 A1 | 3/2010 | Kangas |
| 2010/0130815 A1 | 5/2010 | Gross et al. |
| 2010/0233021 A1 | 9/2010 | Sliwa et al. |
| 2010/0305715 A1 | 12/2010 | Mathis |
| 2011/0276121 A1 | 11/2011 | Levine |
| 2012/0285607 A1* | 11/2012 | Gellman ............... A61F 2/88 156/143 |
| 2013/0060238 A1 | 3/2013 | Lavelle |
| 2016/0279317 A1* | 9/2016 | Gale ................... A61M 1/3655 |
| 2016/0302911 A1* | 10/2016 | Soletti ................. A61L 27/18 |
| 2016/0361152 A1* | 12/2016 | Barron ................. A61F 2/04 |

FOREIGN PATENT DOCUMENTS

| | | |
|---|---|---|
| DE | 20 2005 001 416 U1 | 3/2005 |
| EP | 0 054357 B1 | 11/1981 |
| EP | 0 213 748 A1 | 7/1986 |
| EP | 0 266 091 A2 | 10/1987 |
| EP | 0 418 381 A1 | 9/1988 |
| EP | 0 365 269 A1 | 10/1989 |
| EP | 0 365 269 B1 | 10/1989 |
| EP | 0 516 189 A1 | 10/1989 |
| EP | 0 516 189 B1 | 10/1989 |

(56) References Cited

FOREIGN PATENT DOCUMENTS

| | | |
|---|---|---|
| EP | 0 672 394 A1 | 2/1995 |
| EP | 0 806 189 A1 | 5/1997 |
| EP | 1 609 494 A1 | 12/2005 |
| FR | 2 512 678 | 9/1982 |
| GB | 2 127 294 A | 9/1983 |
| GB | 2 426 199 A | 11/2006 |
| JP | 2004 248886 A | 2/2003 |
| WO | WO 90/14804 | 5/1990 |
| WO | WO 93/25265 | 6/1993 |
| WO | WO 97/24081 | 12/1996 |
| WO | WO 97/36536 | 4/1997 |
| WO | WO 98/09667 | 3/1998 |
| WO | WO 00/66032 | 4/2000 |
| WO | WO 00/74577 A1 | 12/2000 |
| WO | WO 01/91668 A1 | 5/2001 |
| WO | WO 03/079930 A1 | 3/2003 |
| WO | WO 2005/096915 A1 | 3/2005 |
| WO | WO 2007/027830 A1 | 8/2007 |
| WO | WO 2009/023720 A1 | 8/2008 |
| WO | WO 2010/063998 A2 | 10/2010 |

OTHER PUBLICATIONS

Tenke, P., et al., Bacterial biofilm formation on urologic devices and heparin coating as preventive strategy, International Journal of Antimicrobial Agents 23S1 (2004) pp. S67-S74.

Wah, Tze M. and Irving, Henry C.; "A New Design for a Metallic Stent for the Management of Malignant Ureteral Obstruction"; European Renal & Genito-Urinary Disease 2006; pp. 93, 94, 96.

Flexor DL® Dual Lumen Ureteral Access Sheath, https://www.cookmedical.com/product/-/catalog/display?ds=uro_fusdl_webds, Sep. 30, 2013, 2 pgs.

Flexor® Ureteral Access Sheath, https://www.cookmedical.com/product/-/catalog/display?ds=uro_fus_webds, Sep. 30, 2013, 2 pgs.

Cook® 810 Set, https://www.cookmedical.com/product/-/catalog/display?ds=uro_cook810_webds; Sep. 30, 2013, 1 pg.

Extended European Search Report for App. No. 15190347.3, dated Mar. 3, 2016, 8 pp.

Communication Pursuant to Article 94(3) EPC for EPO application No. 15 190 347.3, dated Nov. 24, 2016, 6 pp.

* cited by examiner

ELONGATE MEDICAL DEVICE

CROSS-REFERENCE TO RELATED APPLICATIONS

This application claims priority from U.S. Provisional Application No. 62/068,067, filed on Oct. 24, 2014, the entirety of which is hereby fully incorporated by reference herein.

TECHNICAL FIELD

This disclosure relates to medical devices that may be placed within body for a long term medical purpose. For example, the disclosure relates to stents that are configured for long term placement in a patient's urinary system, such as a patient's ureter, to provide patency therethrough in clinical situations where the patency through the urinary system is compromised or blocked due to external forces, for example due to tumors or growths proximate to the ureter.

BRIEF SUMMARY

A representative embodiment of the disclosure is provided. The embodiment includes a stent. The stent includes an elongate member extending between a distal end portion and a proximal end portion with a central portion disposed therebetween, the elongate member defining a lumen defined therethrough, the central portion of the elongate member is defined from a wire that is coiled to define a plurality of neighboring and longitudinally aligned coils, the plurality of coils collectively defining the lumen therethrough, the plurality of coils are configured such that neighboring coils are closely aligned. The central portion further comprises a jacket disposed around a majority of an outer circumference of the plurality of coils, the jacket defining opposing first and second longitudinal edges that extend along the length of the central portion, and an elongate gap between opposing first and second longitudinal edges exposing portions of each of the plurality of coils aligned therewith, wherein the elongate gap allows for fluid communication from within or into the lumen through spaces between neighboring coils and through the elongate gap. Each of the distal end portion and the proximal end portion of the member include respective apertures at a tip thereof, each of the respective apertures allow communication into and through the lumen.

Another representative embodiment of the disclosure is provided. The disclosure includes a stent. The stent includes an elongate member extending between a distal end portion and a proximal end portion with a central portion disposed therebetween, the elongate member defining a lumen defined therethrough, the central portion of the elongate member is defined from a wire that is coiled to define a plurality of neighboring and longitudinally aligned coils, the plurality of coils collectively defining the lumen therethrough, the plurality of coils are configured such that neighboring coils are closely aligned. The central portion further comprises a jacket disposed around a majority of an outer circumference of the plurality of coils, the jacket defining opposing first and second longitudinal edges that extend along the length of the central portion, and an elongate gap between opposing first and second longitudinal edges exposing portions of each of the plurality of coils aligned therewith, wherein the elongate gap allows for fluid communication from within or into the lumen through spaces between neighboring coils and through the elongate gap. Each of the distal end portion and the proximal end portion of the member include respective apertures at a tip thereof, each of the respective apertures allow communication into and through the lumen, and the elongate gap extends along the central portion and does not extend along at least one of the distal end portion and the proximal end portion, and wherein the elongate gap is helical along its length.

Yet another representative embodiment of the disclosure is provided. The embodiment includes a stent. The stent includes an elongate member extending between a distal end portion and a proximal end portion with a central portion disposed therebetween, the elongate member defining a lumen defined therethrough, the central portion of the elongate member is defined from a wire that is coiled to define a plurality of neighboring and longitudinally aligned coils, the plurality of coils collectively defining the lumen therethrough, the plurality of coils are configured such that neighboring coils are closely aligned. The central portion further comprises a jacket disposed around a majority of an outer circumference of the plurality of coils, the jacket defining opposing first and second longitudinal edges that extend along the length of the central portion, and an elongate gap between opposing first and second longitudinal edges exposing portions of each of the plurality of coils aligned therewith, wherein the elongate gap allows for fluid communication from within or into the lumen through spaces between neighboring coils and through the elongate gap. Each of the distal end portion and the proximal end portion of the member include respective apertures at a tip thereof, each of the respective apertures allow communication into and through the lumen. The elongate gap extends along the central portion and does not extend along at least one of the distal end portion and the proximal end portion, and further comprising a second wire disposed along the central portion, wherein a first end of the second wire is fixed to one or more of the plurality of coils at a distal end portion of the central portion, and a second end of the second wire is fixed to one or more of the plurality of coils at a proximal end portion of the central portion.

Advantages of the disclosed devices will become more apparent to those skilled in the art from the following description of embodiments that have been shown and described by way of illustration. As will be realized, other and different embodiments are contemplated, and the disclosed details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Figure 1:
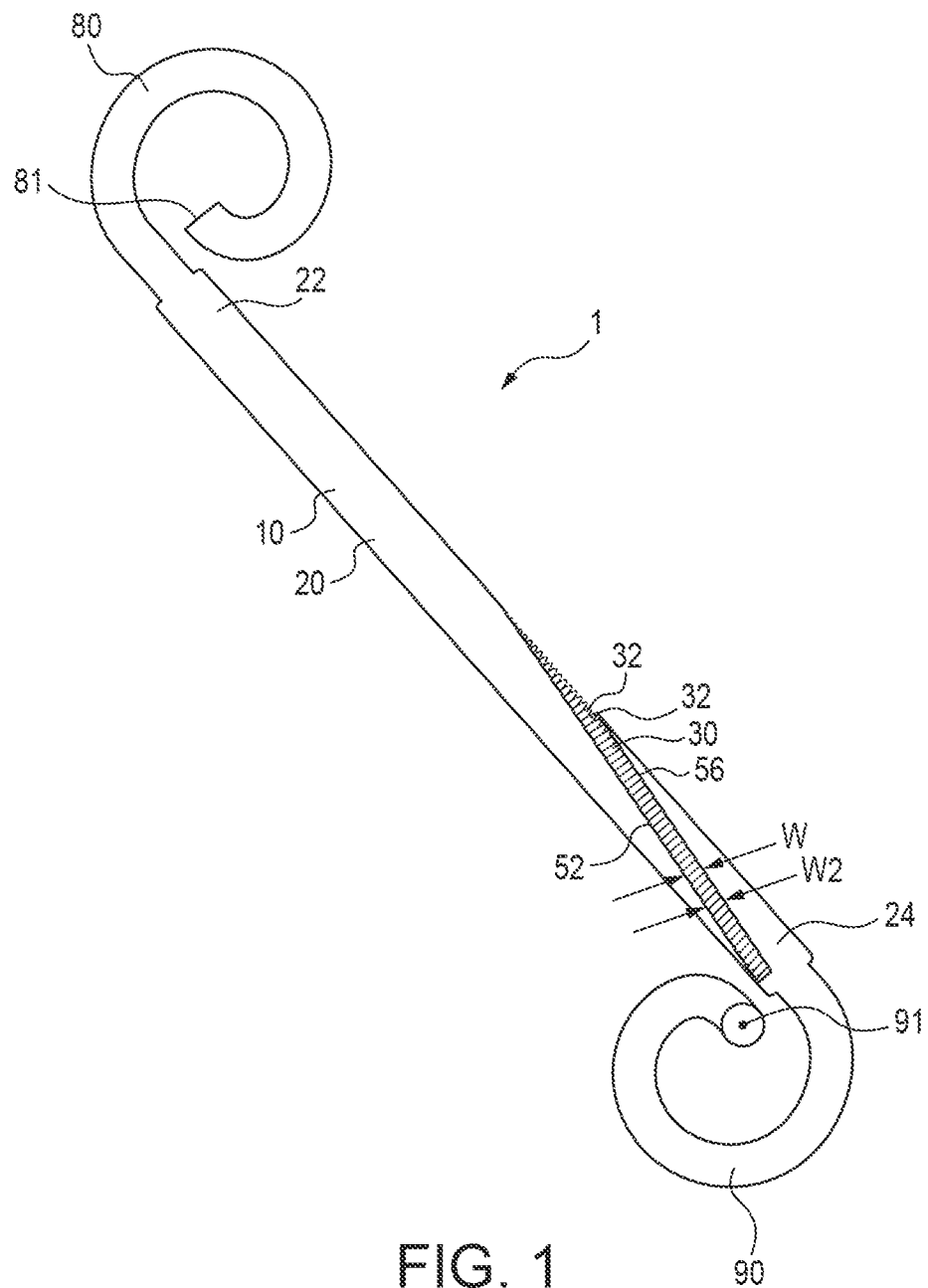
FIG. 1 is a top view of a stent with the distal and proximal end portions in a non-linear configuration.

Turning now to the figures, a medical device 1, such as an elongate stent 10 is provided. The stent 10 extends between a distal end portion 80 and a proximal end portion 90 and encloses a lumen 11 therethrough. In some embodiments, the lumen 11 extends along the entire length of the stent 10 such that an elongate member, such as a wire guide (depicted schematically as 2000 in FIG. 1a), obturator, dilator, or the like can slidably extend through the entire length of the stent 10, through the lumen 11 and out of apertures 81, 91 that may be disposed at the tips of each of the distal and proximal end portions 80, 90. The stent 10 may include a central portion 20 that is disposed between the distal and proximal end portions 80, 90 with the lumen 11 continuously extending from the central portion 20 and in opposite directions into each of the distal and proximal end portions 80, 90.

Figure 1A:
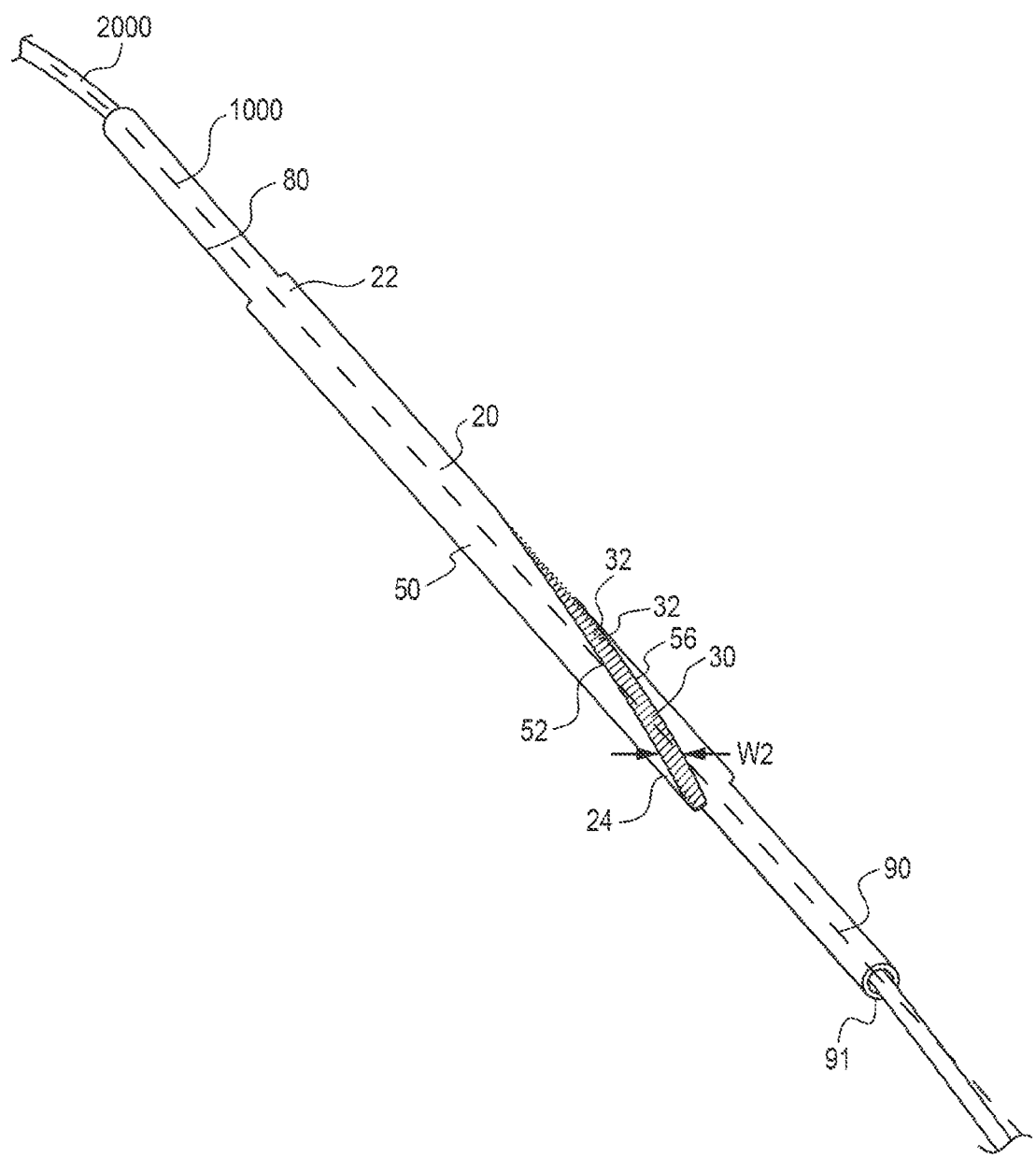
FIG. 1*a* is the view of FIG. 1 with the distal and proximal end portions in a relatively straight configuration with a wire guide extending through a lumen of the stent.

In some embodiments, the central portion 20 may be generally straight, such as extending along a straight longitudinal axis 1000 (FIG. 1a). In some embodiments, the central portion may be exactly parallel to a straight longitudinal axis 1000, while in other embodiments, the central portion 20 may be generally parallel to the longitudinal axis 1000, such as with portions that are slightly arcuate (such as with relatively large radiuses of curvature, such as with a radius of curvature that is 10, 15, 20 or more times greater than the diameter of the central portion 20), but with the entire central portion 20 generally following the longitudinal axis 1000. The central portion 20 may be sufficiently flexible to be able to bend when deployed within a patient to follow the contour of the portion of the anatomy deployed therewithin, such as through a patient's ureter, urethra, bile duct, pancreatic duct, esophagus, colon, arteries, veins, or the like, while still maintaining the lumen 11 open to allow liquid to flow through the lumen 11 when deployed.

As shown in FIG. 1, one or both of the distal and proximal end portions 80, 90 may include a non-linear geometry, such as an arcuate geometry, in some embodiments along a portion of the distal or proximal end portion 80, 90 less than the entire length of the respective portion, or the end potions 80, 90 may be arcuate for the entire length of the respective portion. In some embodiments, one or both of the distal and proximal end portions 80, 90 may be biased into the arcuate geometry. In some embodiments one or both of the distal and proximal end portions 80, 90 are shaped to create "pit-tails," j-curves, or other shapes that are well adapted to retain a stent 10 in position within a desired portion of the anatomy. For example, when the stent 10 is configured to be clinically deployed through a ureter, the distal end portion 80 when deployed is configured to form a pig-tail that is retained within a patient's kidney, and the proximal end portion 90 when deployed is configured to form a pig-tail that is retained within a patient's bladder. As is well understood, these non-linear features received within these or other specific portions of a patient's anatomy may be configured to retain the stent 10 where deployed to prevent undesired translation or other movement with a patient.

The distal and proximal end portions 80, 90 may be sufficiently flexible to be deformed from the non-linear (such as arcuate) geometry to a relatively straight geometry, where the respective portion 80, 90 extends along the longitudinal axis 1000 of the central portion 20, as shown in FIG. 1a. The respective portion 80, 90 may be urged into the relatively straight geometry when an elongate member (such as a wire guide or the like) extends therethrough, specifically through portions of the lumen 11 that extend through the respective end portion 80, 90. In some embodiments, one or both of the distal and proximal end portions 80, 90 are configured such that the lumen 11 is patent (and sufficiently flexible and kink resistant) to allow fluid flow therethrough when in both the non-linear configuration and the elongate configurations depicted in FIGS. 1 and 1a, respectively.

Figure 2:
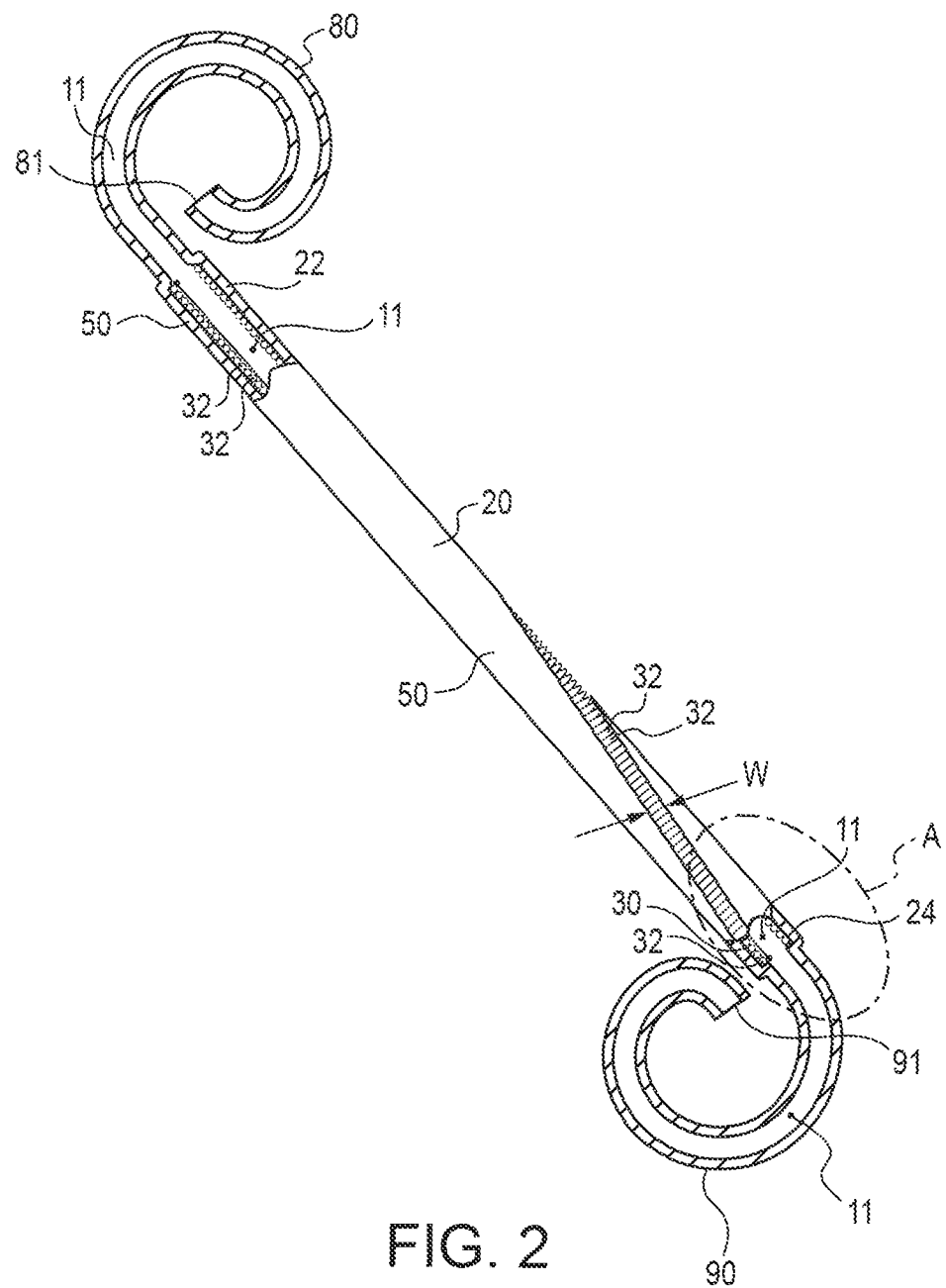
FIG. 2 is the view of FIG. 1 with portions of the stent shown in cross-section.
Figure 2A:
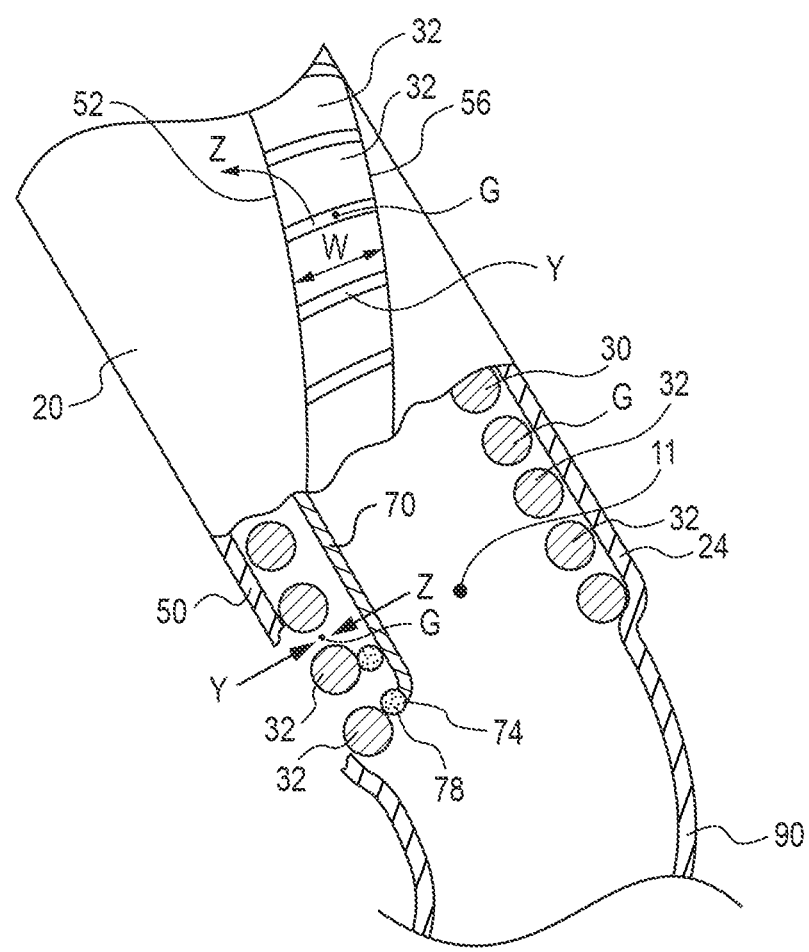
FIG. 2*a* is the view of detail A of FIG. 2.

The central portion 20 extends between a distal end portion 22 and a proximal end portion 24, with the respective end portion 22, 24 of the central portion 20 forming a transition with the respective distal and proximal end portions 80, 90 of the stent 10. The central portion 20 may be defined by a wire 30 that is tightly coiled to form a plurality of neighboring coils 32 that collectively define the lumen 11 therethrough. The coiled wire 30 may be configured such that the device 10 is substantially flexible such that neighboring coils 32 (FIG. 2A) contact each other at some positions around the circumference of the central portion 20 and at other locations around the circumference define a small space G therebetween. The central portion 20, and specifically the wire 30 forming the plurality of neighboring coils 32 is configured such that fluid flow through the lumen 11 may leave the central portion 20 (through the gap W, discussed below) through the spaces G in the direction Z, or fluid outside of the central portion 20 (and within the lumen of the anatomy where the central portion 20 is deployed) may flow through the gap W, the spaces G, and into the lumen in the direction Y (FIG. 2A).

In some embodiments and as shown in FIGS. 2a, 4a, 4b, and 5, the central portion 20 may include a second wire 70, which may function as a safety wire (discussed in further detail below) that extends between distal and proximal ends 72, 74. The second wire 70 may be aligned with respect to the central portion 20 such that the distal end 72 is fixed to the distal end portion 22 of the central portion 20 and the proximal end 74 is fixed to the proximal end portion 24 of the central potion 20. The second wire 70 may extend within the lumen 11 through the central portion 20, or the second wire 70 may extend along the outer surface of the coils 32. The opposite ends 72, 74 of the second wire 70 may be fixed to the opposite distal and proximal end portions 22, 24 with a weld joint (schematically depicted as 78 in FIG. 2A), a mechanical crimp joint, a locking structure (such as locking fitting), with adhesive or with a combination of these or other joining structures or methods known in the art. The second wire 70 may be a material that is substantially unstretchable such that when pulled in tension, or bent traversely, the length of the second wire 70 does not significantly change.

Figure 4C:
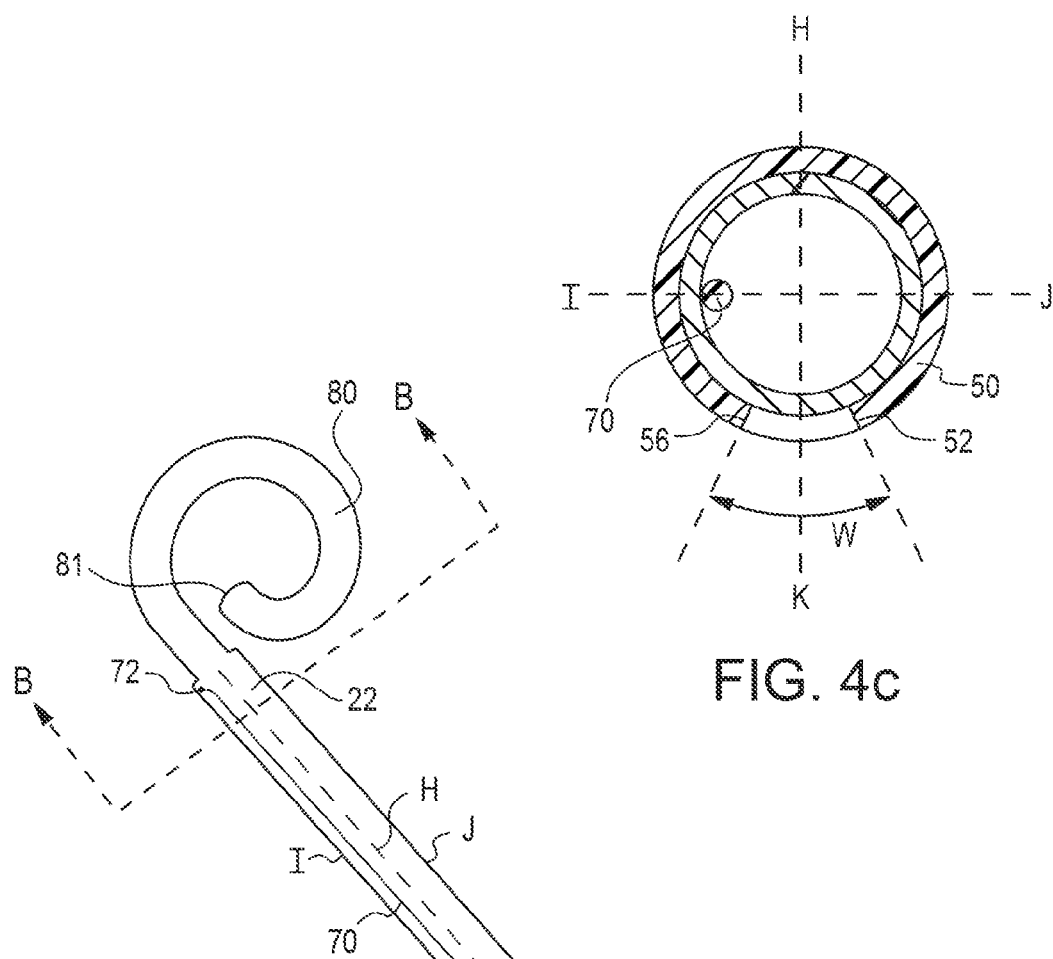
FIG. 4*c* is a view of section B-B of FIG. 4*a*.
Figure 4A:
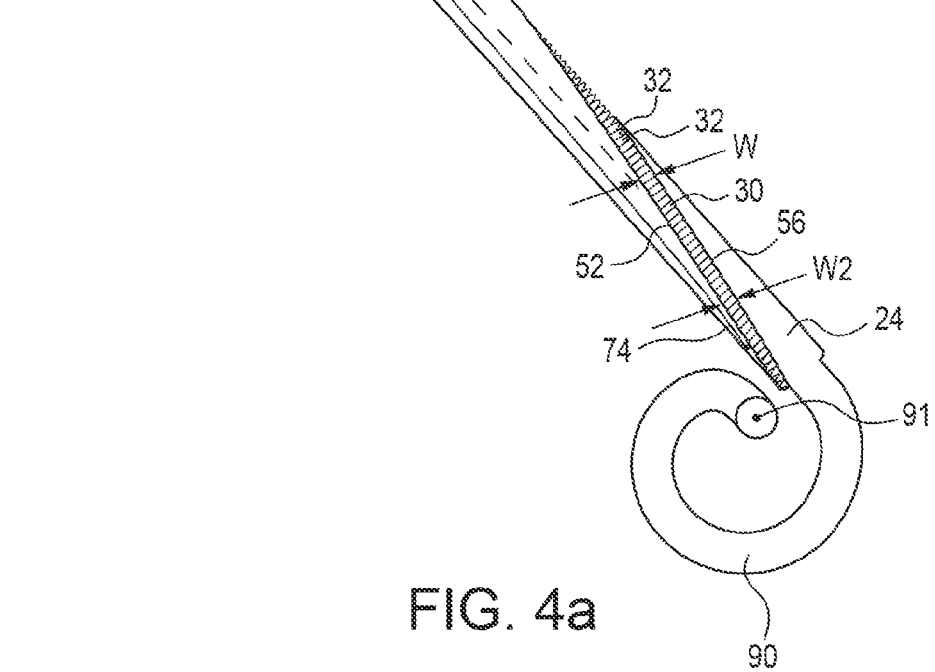
FIG. 4*a* is view of FIG. 1 showing the second wire extending along the length of the central portion of the stent.
Figure 4D:
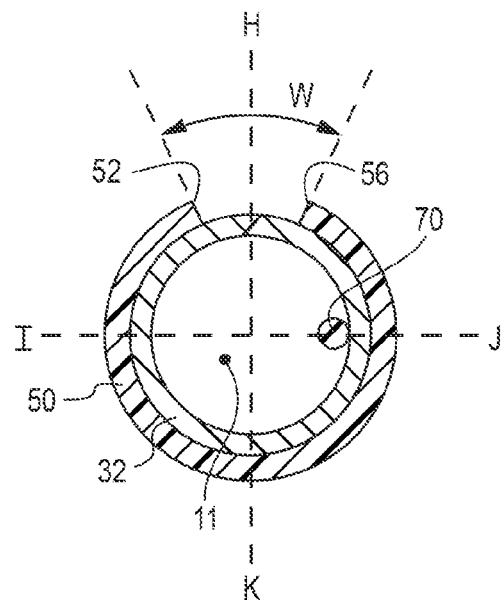
FIG. 4*d* is a view of section C-C of FIG. 4*b*.

The second wire 70 may be a "safety wire" which is mounted with respect to the central portion 20 to prevent the elongation or stretching of the central portion 20. The second wire 70 may provide a biasing force to the central portion 20 to urge the central portion to return to its nominal elongate geometry. In some embodiments and as shown schematically in FIG. 4a, the second wire 70 may be fixed to the central portion 20 such that it is normally aligned (and biases the central portion 20 to return to an alignment) along the same circumferential position along the length of the central portion 20. For example, as shown schematically in FIGS. 4a and 4c, the second wire 70 may normally be positioned proximate to an inner surface of each of the neighboring coils 32 proximate to a location schematically depicted as direction "I" along the length of the central portion 20. If the central portion 20 is twisted along its length as schematically shown with force X in FIG. 4b, the second wire 70 may also twist along its length such that (for example) the distal end 72 may be disposed at direction J (FIGS. 4c and 4d) while the proximal end 74 is disposed at direction I (FIG. 4a). Because the second wire 70 is placed in tension when the central portion 20 of the stent is twisted, when the force establishing the twist in the central portion 20 is released the second wire 70 urges the central portion to un-twist (in the opposite direction of X, FIG. 4b) such that the second wire 70 attempts to return to the straight orientation, such as in direction I along its length.

The central portion 20 may further include a jacket 50, which may extend along the entire central portion 20 and, in some embodiments, may extend continuously beyond the distal and proximal end portions 22, 24 of the central portion 20 to define the distal and proximal end portions 80, 90 of the stent 10. The jacket 50 may be disposed along the central portion 20 and along an outer surface of each of the plurality of adjacent coils 32. In some embodiments, the jacket 50 may include portions that extend between the plurality of gaps G between neighboring coils 32 and may reach toward or to the inner surface of the plurality of coils 32, such that the jacket 50, where provided, combines with the coils 32 to establish the lumen 11.

In some embodiments, the jacket 50 may be disposed around a majority of the outer circumference of the central portion 20 but may be disposed to form at least one gap W upon the central portion 20 to expose a portion of each of the coils 32. The gap W may extend along the entire length of the central portion 20, while in other embodiments, the gap W may extend only along one or more portions of the length of the central portion 20, including embodiments with several gaps W disposed along the length of the central portion 20 with the remaining portion(s) of the central portion 20 formed with the jacket 50 formed around the entire circumference of the central portion 20.

The gap W may be defined between opposite first and second longitudinal edges 52, 56 of the jacket 50, and specifically the gap W may be formed where there is no jacket 50 disposed over the plurality of coils 32. As shown schematically in FIG. 2A, the gap W is disposed to allow fluid to flow from the lumen 11 and out of the stent 10 in the direction Z, or flow from outside of the stent 10 and into the lumen 11 in the direction Y.

In some embodiments, the gap W may be formed with a helical profile along the length of the central portion 20, such that the position of the gap W upon the circumferential surface of the central portion 20 changes (and in some embodiments continuously changes) along the length of the central portion 20. In some embodiments shown in FIG. 1, the position of the gap W may rotate about 180 degrees from the distal end portion 22 to the proximal end portion 24 of the central portion. In other embodiments shown in FIG. 5, the gap W may rotate nominally 360 degrees along the length of the central portion 20. In other embodiments, the gap W may rotate about other angular distances, such as about 0 degrees (i.e. a straight gap W), 45, 90, 135, 235, 270, 315, 540, 720 degrees, or even higher angular distances, or at any angular distance within a range of 0 degrees and 720 degrees inclusive of all angles therewithin. As used herein, the term "about" is defined as plus or minus 5 degrees from the value noted.

Figure 4B:
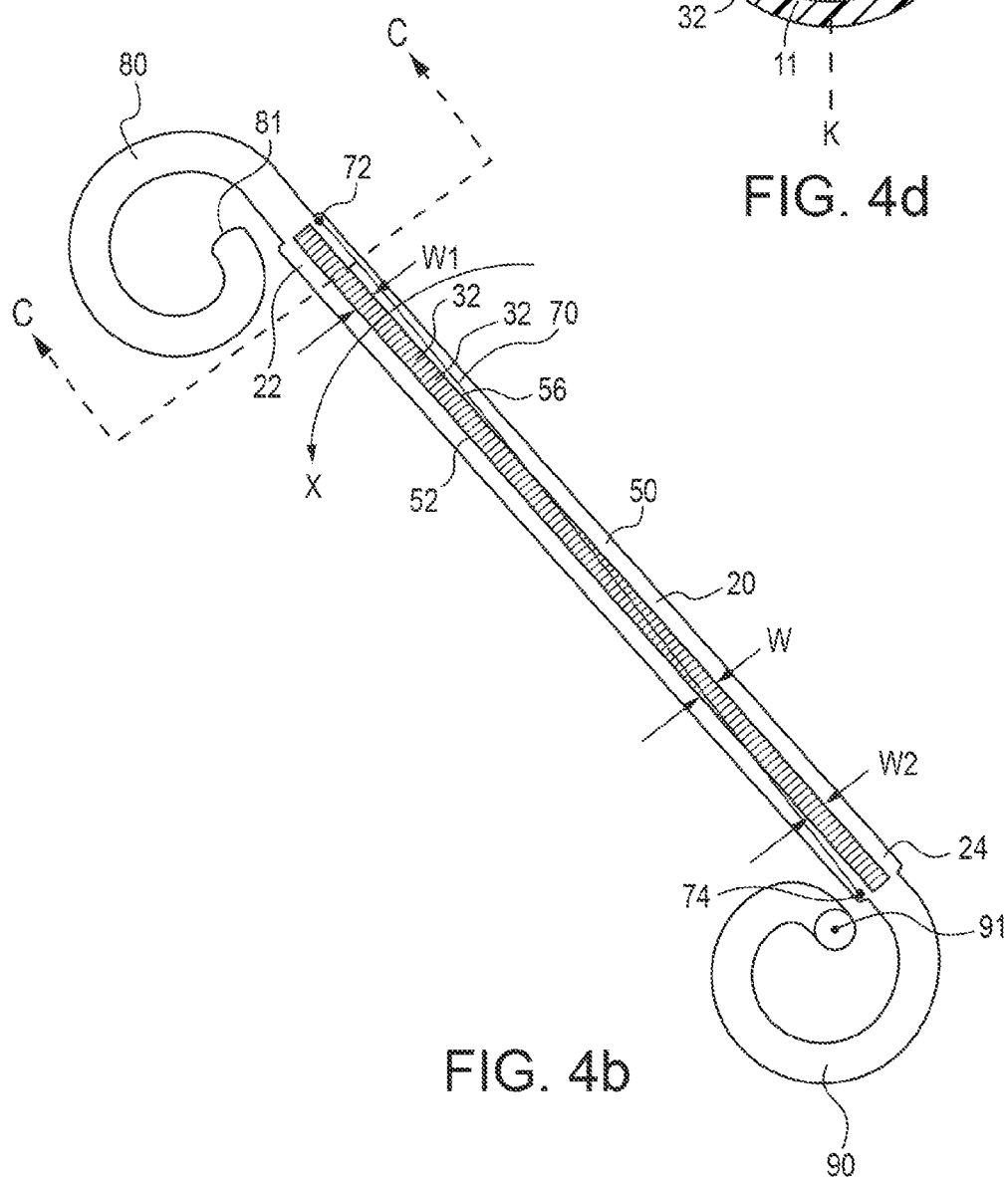
FIG. 4*b* is the view of FIG. 4*a* showing the stent after having been twisted in the direction X about 180 degrees.
Figure 5:
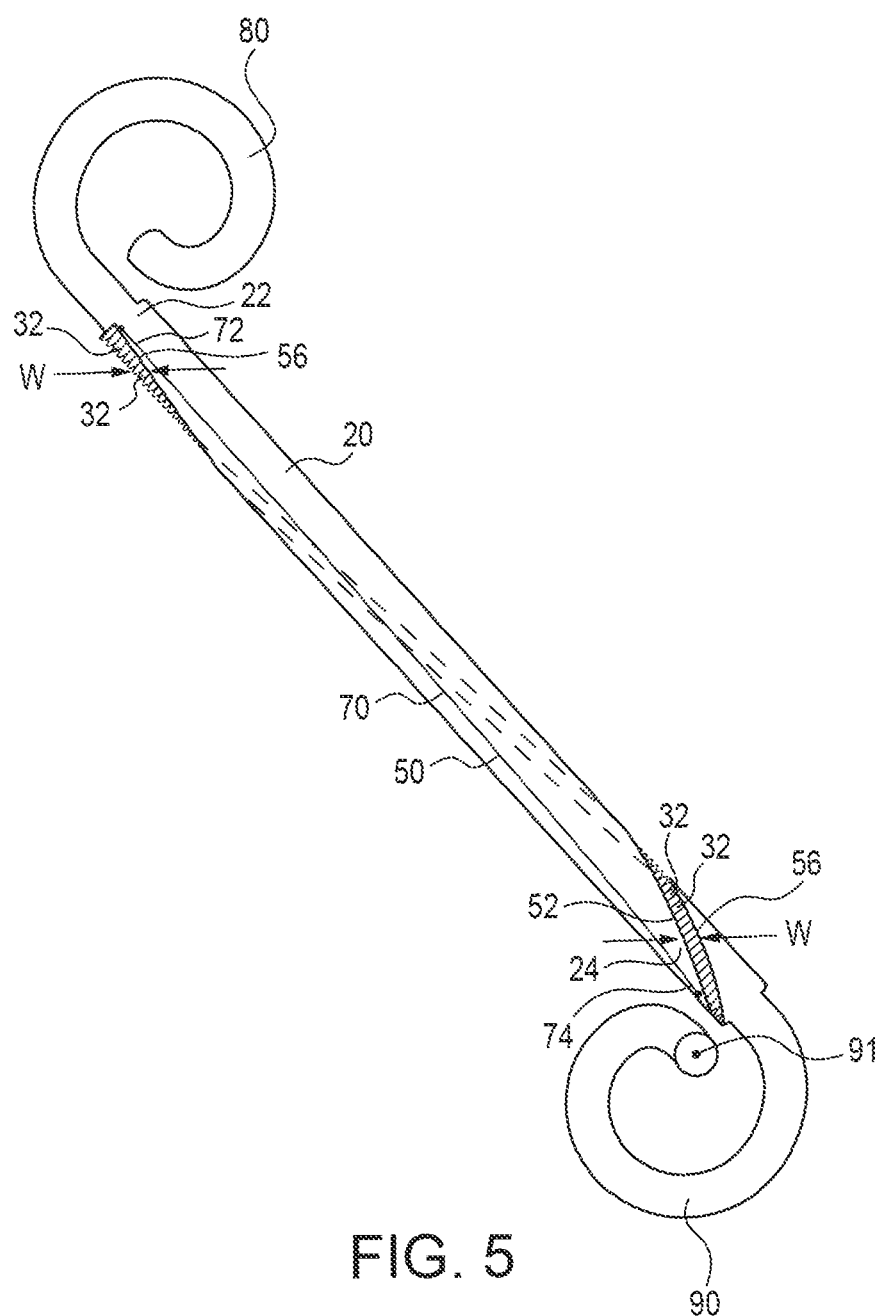
FIG. 5 is the view of FIG. 1 with a gap in the jacket helically extending about 360 degrees along the length of the central portion of the stent.

In some embodiments, the central portion 20 may be twisted about its length (such as e.g. in the direction X of FIG. 4b) such that the position and the angular distance of the gap W changes as the central portion 20 is twisted. For example, FIG. 4b depicts an embodiment where the central portion 20 of the stent 10 has been twisted in the direction X such that the gap W extends along a straight line from an initial (untwisted) orientation (FIG. 4a) where the gap W twisted about 180 degrees between the distal and proximal end portions 22, 24 of the central portion 20. As discussed above, in embodiments with the second wire 70, the central portion 20 may be urged to twist in the direction opposite from direction X if the twisting forces upon the stent 10 are released, as urged by the second wire 70. In other embodiments where the central portion 20 is formed with the gap W normally twisting about 360 degrees (FIG. 5), the central portion 20 may be twisted such that the gap W twists about 180 degrees (FIG. 1), and further twisted such that the gap W is substantially straight (i.e. 0 degrees, as depicted in FIG. 4b)

In some embodiments, the central portion 20 may include two or more gaps W that extend along the length (or portions of the length) thereof. For example, two gaps W may be provided on opposite sides of the central portion 20. The two gaps W may each extend at the same angular direction and pitch such that the gaps W are constantly on opposite circumferential portions of the central portion 20 along the length of the central portion 20. In other exemplary embodiments with multiple gaps W, the gaps W may be extended in opposite helical directions, such that the gaps W may periodically cross. In still other exemplary embodiments, one gap W may be straight and another gap may extend in a helical direction. One of ordinary skill in the art with a thorough review of this specification will understand that a multitude of different geometries and numbers of gaps W may be provided upon the central portion 20 of the stent to allow for differing liquid flow profiles in the directions Z and/or Y at different positions along the length of the central portion 20, and based upon the clinical need of flow into or out of the lumen 11 at different anatomical positions of a deployed stent 10.

Figure 3:
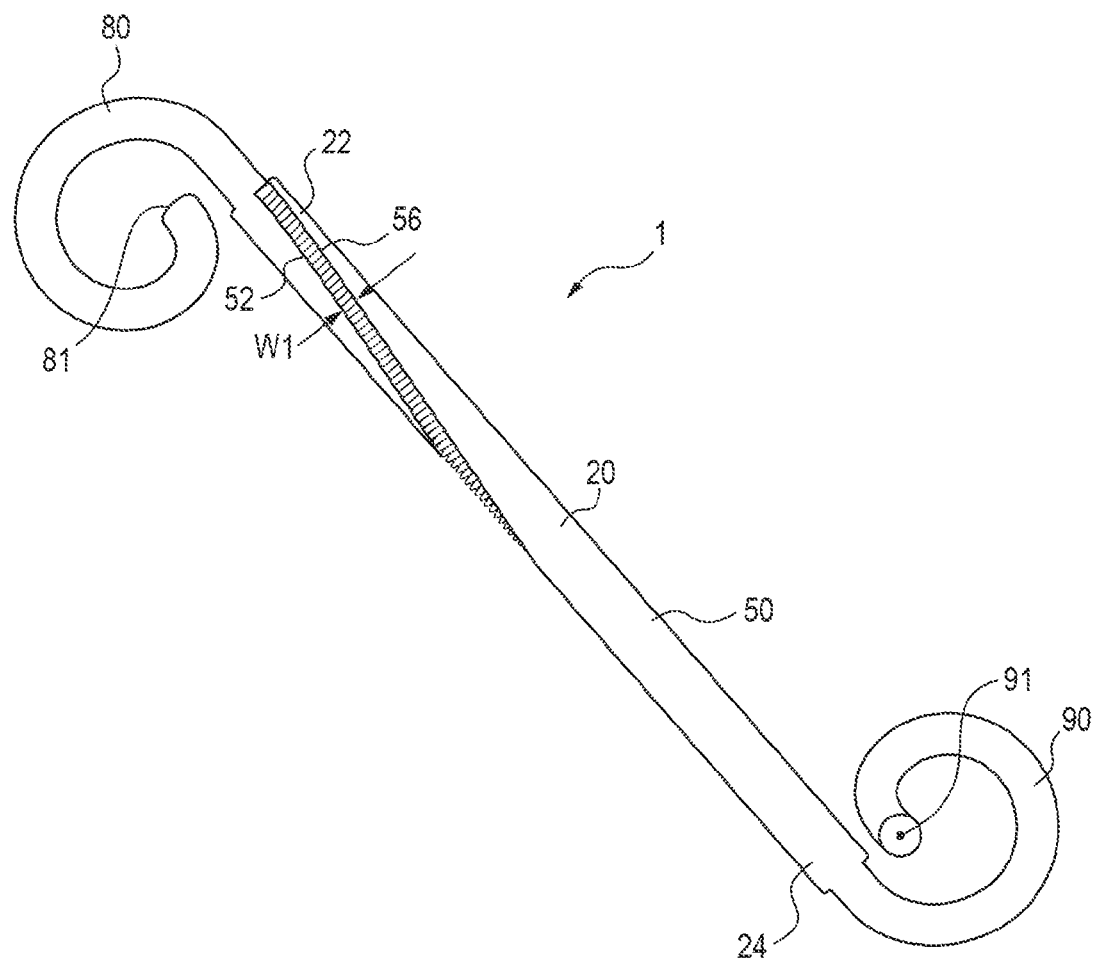
FIG. 3 is a back side view of the stent of FIG. 1.

In some embodiments, the gap W may have a constant width (as defined by the arc length of the circumference of the central portion between the first and second longitudinal edges 52, 56) along the length of the central portion 20 (or in embodiments where the gap W does not extend along the entire length, along the portions of the central portion 20 with the gap W). In other embodiments, the width of the gap W may change along the length of the central portion 20, such as a continuously (or step changing) increase in the width of the gap W from the distal end portion 22 to the proximal end portion 24, or in other embodiments, a continuously (or step changing) decrease in the width from the distal to the proximal end portions 22, 24. As shown schematically in FIGS. 1 and 3, the gap W at the distal end portion 22 is depicted as W1, and the gap at the proximal end portion 24 is depicted as W2. In some exemplary embodiments, the gap W may have a width of 30 degrees of arc length along the length of the central portion 20. In other embodiments, the width of the gap W may be 45, 60, 75, or 90 degrees, or within the range of about 15 degrees to about 90 degrees, inclusive of all angles within this range. As used herein, the term "about" is defined at plus or minus 5 degrees from the value noted. As with the different potential ranges of curvature (or the different potential of number of gaps W greater than one), one of ordinary skill with a thorough review of this specification will be able to determine the appropriate size the width of the gap W (in combination with the other variables of the gap W, such as curvature of the gap, or the number of gaps) to achieve the appropriate flow through the gap(s) W along the length of the central portion 20 and in conjunction with the desired flow profile at the clinical location where the stent 10 will be deployed.

In some embodiments, the jacket 50 may extend distally and/or proximally beyond the opposed ends of the central portion 20 to define one or both of the distal end portion 80 and the proximal end portion 90, discussed above. The jacket 50 may form the portion of the lumen 11 through the distal and proximal end portions 80, 90 and due to the continuity between the end portions 80, 90 and the central portion 20, the lumen extends through the entire length of the stent and ultimately out of apertures 81, 91 at the tips of the respective distal and proximal end portions 80, 90. In some embodiments, the jacket 50 may be made of a material (and with a sufficient wall thickness) to maintain the lumen 11 therethrough when both in the normal arcuate configuration (e.g. FIG. 1) and when in the elongate configuration (FIG. 1a) without kinking, inelastically stretching or any other permanent deformation.

In some embodiments, the jacket 50 (or a portion of the jacket 50) may be made from a polymer or other medically acceptable material that forms the functional requirements of the jacket 50 discussed above. The jacket 50 may include portions that are coated with drugs, or configured for drug elution (such as anti-spasmodics, analgesics, anti-inflamatory, etc.), hydrophobic or hydrophilic coatings, anti-microbial, or anti-bacterial coatings, anti-encrustation, or other coatings or drugs that may be clinically beneficial for a stent to be deployed within a certain portion of the anatomy and for a certain clinical purpose. In some embodiments the material forming the jacket 50 (i.e. uncoated) may include one or more features (such as hydrophobic, hydrophilic, anti-encrustation, etc.)

In some embodiments, all or portions of the wire 30 forming the coils 32 of the central portion 20 may be embedded within the jacket 50. In some embodiments, the jacket 50 may be disposed about the inner surface of the neighboring coils 32, such that the inner surface of the jacket 50 (where provided) forms the surface of the lumen 11.

The jacket 50 may be formed upon the stent with an extrusion process, with the plurality of coils 32 (and the safety wire 70, when provided) co-extruded with the jacket 50. The gap W may be formed by removing portions of the jacket 50 along the length of the central portion 20, or alternatively, the gap W may be created by extruding (or forming the jacket 50 by other methods) without material in the position where the gap W is desired.

The wire 30 forming the plurality of coils 32 may be made from a metal. In some embodiments, the metal may be an alloy of minimal or low magnetic properties, such as MP35N, MP159, Astroloy M, Inconel 625, 316 stainless steel 35N LT Biodur 108, titanium, or Hastelloy S. In some embodiments, the wire 30 may be made from a metal, and alloys of metals with the strength such that the coils 32 maintain their shape (and specifically the patency of the lumen 11) when placed in local compression by the surroundings.

While the preferred embodiments of the disclosure have been described, it should be understood that the disclosure is not so limited and modifications may be made without departing from the invention. The scope of the invention is defined by the appended claims, and all devices that come within the meaning of the claims, either literally or by equivalence, are intended to be embraced therein.

The invention claimed is:

1. An stent, comprising:
an elongate member extending between a distal end portion and a proximal end portion with a central portion disposed therebetween, the elongate member defining a lumen defined therethrough, the central portion of the elongate member is defined from a wire that is coiled to define a plurality of neighboring and longitudinally aligned coils, the plurality of coils collectively defining the lumen therethrough, the plurality of coils are configured such that neighboring coils are closely aligned;
the central portion further comprises a jacket disposed around a majority of an outer circumference of the plurality of coils, the jacket defining opposing first and second longitudinal edges that extend along the length of the central portion, and an elongate gap between opposing first and second longitudinal edges exposing portions of each of the plurality of coils aligned therewith, wherein the elongate gap allows for fluid communication from within or into the lumen through spaces between neighboring coils and through the elongate gap;
wherein each of the distal end portion and the proximal end portion of the member include respective apertures at a tip thereof, each of the respective apertures allow communication into and through the lumen.

2. The stent of claim 1, wherein at least one of the distal end portion and the proximal end portion is biased to a first arcuate configuration and is sufficiently flexible to be aligned in a second elongate configuration wherein the respective end portion extends substantially along a longitudinal axis that extends through the central portion.

3. The stent of claim 1, wherein the distal end portion and the proximal end portion of the elongate member are each biased to a first arcuate configuration and are each sufficiently flexible to be aligned in a second elongate configuration, wherein the distal end portion and the proximal end portion are defined by the jacket disposed along the central portion, wherein portions of the jacket that define the proximal and distal end portions extend around an entire circumference of the respective distal and proximal end portions.

4. The stent of claim 1, wherein the elongate gap extends along the central portion and does not extend along at least one of the distal end portion and the proximal end portion.

5. The stent of claim 1, wherein the elongate gap is helical along its length.

6. The stent of claim 5, wherein the elongate gap rotates about 180 degrees along the length of the central portion.

7. The stent of claim 6, wherein the central portion is biased into an orientation such that the gap rotates about 180 degrees along the length of the central portion, and wherein the central portion may be twisted into an orientation wherein the elongate gap is substantially straight along the length of the central portion.

8. The stent of claim 5, wherein the elongate gap rotates about 360 degrees along the length of the central portion.

9. The stent of claim 8, wherein the central portion is biased into an orientation such that the gap rotates about 360 degrees along the length of the central portion, and wherein the central portion may be twisted into an orientation where the elongate gap rotates about 180 degrees along the length of the central portion.

10. The stent of claim 9, wherein the central portion may be twisted to an orientation where the elongate gap is substantially straight along the length of the central portion.

11. The stent of claim 1, wherein the elongate gap has a constant arc length along its length.

12. The stent of claim 1, wherein the elongate gap has an increasing arc length from a distal end portion of the central portion to a proximal end portion of the central portion.

13. The stent of claim 1, wherein at least a portion of the elongate gap has an arc length of about 30 degrees.

14. The stent of claim 1, wherein at least a portion of the elongate gap has an arc length of about 45 degrees.

15. The stent of claim 1, wherein the jacket extends around an entire circumference of the distal end portion and the proximal end portion.

16. The stent of claim 1, further comprising a second wire disposed along the central portion, wherein a first end of the second wire is fixed to one or more of the plurality of coils at a distal end portion of the central portion, and a second end of the second wire is fixed to one or more of the plurality of coils at a proximal end portion of the central portion.

17. The stent of claim 16, wherein the second wire is straight, and the connection of the second wire to the one or more coils at each of the proximal and distal end portions establishes a biasing force to return the central portion to an orientation where the second wire is straight when a force that deflected the central portion to an orientation where the second wire was not straight is released.

18. The stent of claim 16, wherein the second wire is disposed within the lumen.

19. A stent, comprising:
an elongate member extending between a distal end portion and a proximal end portion with a central portion disposed therebetween, the elongate member defining a lumen defined therethrough, the central portion of the elongate member is defined from a wire that is coiled to define a plurality of neighboring and longitudinally aligned coils, the plurality of coils collectively defining the lumen therethrough, the plurality of coils are configured such that neighboring coils are closely aligned;
the central portion further comprises a jacket disposed around a majority of an outer circumference of the plurality of coils, the jacket defining opposing first and second longitudinal edges that extend along the length of the central portion, and an elongate gap between opposing first and second longitudinal edges exposing portions of each of the plurality of coils aligned therewith, wherein the elongate gap allows for fluid communication from within or into the lumen through spaces between neighboring coils and through the elongate gap;
wherein each of the distal end portion and the proximal end portion of the member include respective apertures at a tip thereof, each of the respective apertures allow communication into and through the lumen;
wherein the elongate gap extends along the central portion and does not extend along at least one of the distal end portion and the proximal end portion, and wherein the elongate gap is helical along its length.

20. A stent, comprising:
an elongate member extending between a distal end portion and a proximal end portion with a central portion disposed therebetween, the elongate member defining a lumen defined therethrough, the central portion of the elongate member is defined from a wire that is coiled to define a plurality of neighboring and longitudinally aligned coils, the plurality of coils collectively defining the lumen therethrough, the plurality of coils are configured such that neighboring coils are closely aligned;
the central portion further comprises a jacket disposed around a majority of an outer circumference of the plurality of coils, the jacket defining opposing first and second longitudinal edges that extend along the length of the central portion, and an elongate gap between opposing first and second longitudinal edges exposing portions of each of the plurality of coils aligned therewith, wherein the elongate gap allows for fluid communication from within or into the lumen through spaces between neighboring coils and through the elongate gap;
wherein each of the distal end portion and the proximal end portion of the member include respective apertures at a tip thereof, each of the respective apertures allow communication into and through the lumen;
wherein the elongate gap extends along the central portion and does not extend along at least one of the distal end portion and the proximal end portion, and further comprising a second wire disposed along the central portion, wherein a first end of the second wire is fixed to one or more of the plurality of coils at a distal end portion of the central portion, and a second end of the second wire is fixed to one or more of the plurality of coils at a proximal end portion of the central portion.

* * * * *